United States Patent [19]

Nakazato

[11] Patent Number: 4,873,269

[45] Date of Patent: Oct. 10, 1989

[54] RESINOUS COMPOSITIONS FOR DENTURE BASE

[75] Inventor: Ryoji Nakazato, Tokorozawa, Japan

[73] Assignee: G-C Dental Industrial Corp., Tokyo, Japan

[21] Appl. No.: 70,701

[22] Filed: Jul. 7, 1987

[30] Foreign Application Priority Data

Jul. 21, 1986 [JP] Japan ................... 61-178958

[51] Int. Cl.⁴ .................................. A61K 6/08
[52] U.S. Cl. ...................... 523/115; 523/120; 525/256; 525/259; 525/263; 106/35
[58] Field of Search ............ 525/256, 263; 523/116, 523/120; 526/205; 106/35

[56] References Cited

U.S. PATENT DOCUMENTS

| | | | |
|---|---|---|---|
| 2,987,500 | 6/1961 | Rossetti | 525/259 |
| 4,001,939 | 1/1977 | Gross | 525/259 |
| 4,396,476 | 8/1983 | Roemer et al. | 523/115 |
| 4,443,587 | 4/1984 | Schmitt et al. | 526/205 |

Primary Examiner—Joseph L. Schofer
Assistant Examiner—Mark D. Sweet
Attorney, Agent, or Firm—Oblon, Spivak, McClelland, Maier & Neustadt

[57] ABSTRACT

A resinous composition for denture base, having improved performance suitable for microwave curing comprises (i) a powdery component containing as the main constituents a methacrylate ester polymer having a mean particle size of 50 to 120 microns, a barbituric acid derivative and an organic peroxide, and (ii) a liquid component containing as the main constituents a monomethacrylate ester monomer, a cross-linking agent and a quaternary ammonium chloride.

20 Claims, 3 Drawing Sheets

RESINOUS COMPOSITIONS FOR DENTURE BASE

BACKGROUND OF THE INVENTION

1. Field of the Invention

The present invention relates to a resinous composition for denture base which is particularly suitable for use in the polymerization method of dentures by irradiation of microwaves (hereinafter called the microwave curing method), but is applicable to the usual polymerization method thereof by heating in water bath.

According to the microwave curing method, a dough-form mixture of resinous compositions for denture base comprising a powdery component and a liquid component is filled and pressurized in a plaster denture negative model previously formed in a glass fiber-reinforced plastic flask (hereinafter simply referred to as the FRP flask), and is then irradiated with microwaves for polymerization. The compositions according to the present invention may be polymerized by the ordinary heat curing method. Especially when the microwave curing method is applied, however, they can be polymerized in a short period of time by irradiation of microwaves, thereby yielding a set product that is homogeneous and free from any porosity, and making it possible to prepare a denture of improved fitting accuracy.

2. Statement of the Prior Art

According to the the ordinary heat curing method for preparing dentures, a previously prepared wax denture is invested in plaster with the use of metallic flask. After the investing plaster is set, the wax is removed to form a denture negative model. Then, a dough-form mixture of a powdery component composed mainly of a methyl methacrylate polymer and a liquid component composed mainly of a methyl methacrylate monomer is filled and pressurized in that model. After heating in hot water of about 70° C. for 30 to 90 minutes, the flask is heated in boiling water for further 30 minutes. The ordinary heat curing method thus requires a time of as long as 60 to 120 minutes, and is therefore inefficient.

Recently, the technique for polymerization making use of microwaves has been developed to achieve such heat curing within a short period of time (see "The Journal of Dental Technology", Vol. 12, No. 8, 1984.8., pp. 965-974), and has begun to be used. According to this technique, a previously prepared wax denture is invested in plaster with the use of FRP flask. After the plastic is set, the wax is removed to obtain a denture negative model formed of plaster. Filled and pressurized in that negative model is a dough-form mixture comprising an ordinary heat-cured type resin for denture base (hereinafter referred to as the heat-curing base resin) consisting of a powdery component composed mainly of a methyl methacrylate polymer and a liquid component composed mainly of a methyl methacrylate monomer. The flask is then placed in a microwave oven for domestic use, wherein it is irradiated with microwaves for 3 to 5 minutes for polymerization.

However, the following problems arise, when it is intended to polymerize a denture by the microwave curing method, using the ordinary heat curing base resin.

(1) Short-time irradiation of microwaves does not allow sufficient polymerization, leaving unpolymerized matters which leads to formation of an inhomogeneouly set product.

(2) Porosity occur in the interior of the resin of a thick portion of the denture.

(3) When a denture including a clasp or a bar or a metal-plated denture is polymerized, porosity occurs in the interior of the resin around the metal.

(4) The polymerized denture deforms with the lapse of time, thus leading to a drop in fitting accuracy.

When the denture containing such problems are clinically used in actual applications, the residual monomer gives a stimulus to the oral mucosa. Further, the denture gives an uncomfortable feeling during mastication due to unsatisfactory fitting caused by their deformation with time and may not fulfill its masticatory function. The presence of internal porosity offers will not cause serious problems that may affect their appearance. However, when an ordinary denture is polymerized, porosity intensively occur in the maximum-occlusal-stress-applied interior of the resin around the alveolar below the base plane of the artificial teeth, which has a grave influence upon the durability of the denture.

When a denture including a clasp or a bar or a metal-plated denture is polymerized, porosity occur in the interior of the resin around the metal. In this case, a further considerable influence is produced upon the durability of that denture, since concentrated stress is applied on the portion where the metal is embedded in the resin, particularly the portion where the metal is maintained by the resin. Thus, when the ordinary heat-curing base resin is polymerized with microwaves, it seems that the denture is polymerized within a short time. As mentioned above, however, the actually obtained denture offers certain problems in view of practical use, and is unsatisfactory. For that reason, there are demanded resinous compositions for denture base having improved performance and, in particular, suitable for use with the microwave curing method.

SUMMARY OF THE INVENTION

In view of the fact that the aforesaid problems arise, when the microwave curing method is used with the ordinary heat-curing base resin, the present invention has been accomplished to solve the aforesaid problems, while taking the advantage of the microwave curing method in which polymerization can be achieved by microwaves within a short time.

More specifically, the present invention provides a resinous composition for denture base, which, as the ordinary heat-curing base resin does, comprises a powdery component and a liquid component which are mixed together into a dough-like resin to be filled and pressurized in a denture negative plaster model prepared in the FRP flask in the same manner as is done with the ordinary heat-curing base resin. The resinous composition according to the present invention is effectively polymerized with the application of short-time irradiation of microwaves to form a set product which in turn provides a denture wherein any porosity is found neither in the interior of the resin of its thick portion nor in the interior of the resin around the metal. The cured product undergoes reduced or limited deformation-with-time, and thus provides a denture of improved fitting accuracy.

It has now been found that, in view of the fact that the problems as mentioned above arise in the case where the ordinary heatcuring base resin is used for the polymerization of dentures by the microwave curing method, the ordinary heat-curing base resin is not essentially suitable for the microwave curing method for the following reasons: Where microwaves are applied to a resin filled in a denture negative model formed of plaster with the use of the FRP flask, the water content contained in the plaster is most effectively heated by such microwaves with a sharp rise in the temperature of the plaster. However, the resin filled in the negative model is lower in heating efficiency than water and, in addition to this, the microwaves have to be transmitted to the internal resin through the plaster having a certain thickness. This leads to considerable energy losses, and makes the rate of rise in temperature rise of the resin much lower than that of the plaster.

It is thus considered that the microwave polymerization of the ordinary heat-curing base resin relies upon the process in which it is mainly effected by indirect heating due to thermal conduction from the rapidly heated plaster, not the process in which the resin per se is rapidly heated by microwaves, thereby starting and proceeding its polymerization reaction. For that reason, when the irradiation time of microwaves is insufficient, or when the thickness of the invested plaster layer is uneven in view of the form of a denture, the rise in temperature of the plaster model becomes uneven as a whole, so that uniform processing of the polymerization of the resin does not take place, thus giving an inhomogeneous set product. When polymerizing a denture including a clasp or a bar or a metal-plated denture, the resin per se of the portion which is located in the shadow of the metal and which microwaves do not reach is not virtually heated by microwaves due to the fact that microwaves do not transmit through the metal, and the plaster of the portion which microwaves do not reach increases in temperature at a more delayed rate. Hence, the resulting set product contains considerable unpolymerized matters and, thus, becomes inhomogeneous. Since the polymerization of the resin starts from its face contacting the rapidly heated plaster, the curing shrinkage is concentrated upon the interior of the resin, leaving internal porosity therein. Heating in this case occurs vigorously from the surface of the resin to produce a considerable number of porosity areas. In addition, when polymerizing a denture including a clasp or a bar or a metal-plated denture, the metal per se is rapidly heated by microwaves, whereby rapid polymerization of the resin contacting it begins to occur. However, the portion of the resin which is not heated in the shadow of the metal is not subjected to polymerization. Due to such a phenomenon, the points of initiation of the polymerization vary markedly, so that porosity are also formed around the metal. Furthermore, considerable internal stresses remain in the set product polymerized and obtained in this manner, since it is inhomogeneous due to the presence of unpolymerized matters, and has been rapidly polymerized from some local points. Since these internal stresses are relieved from the set product with the lapse of time, it deforms to such a degree that its fitting accuracy is unsatisfactory.

Thus, it has been considered that all the causes of the aforesaid problems, which arise from using the ordinary heat-curing base resin with the microwave curing methods, resides in the process of the polymerization which occurs through the process that the resin is unevenly heated from its face contacting the plaster due to indirect heating from the rapidly heated plaster, not through the process that the resin is rapidly heated by irradiation of microwaves for its uniform polymerization from within, and intensive studies have been made for the purpose of obtaining a resinous composition for denture base wherein the resin starts to be rapidly and uniformly polymerized from its inside and is effectively polymerized by irradiation of microwaves. As a result, a novel resinous composition for denture base has been attained, which is polymerized by short-time irradiation of microwaves, provides a homogeneous cured product with no porosity contained therein, and makes it possible to prepare a denture of improved fitting accuracy.

The resinous composition for denture base according to the present invention comprises (i) a powdery component containing as the main constituents a methacrylate ester polymer having an average particle size of 50 to 120 microns, a barbituric acid derivative and an organic peroxide, and (ii) a liquid component containing as the main constituents a monomethacrylate ester monomer, a cross-linking agent and a quaternary ammonium chloride. By using the methacrylate ester polymer as the main constituent of the powdery component and the monomethacrylate ester monomer as the main constituent of the liquid component, it is possible to mix together the powdery and liquid components into a dough-form product and fill and pressurize that product in a denture negative model previously formed of plaster using the FRP flask, as is the case with the ordinary heat-curing base resin. Furthermore, the incorporation of the barbituric acid derivative and organic peroxide into the powdery component and the cross-linking agent and quaternary ammonium chloride into the liquid component assures that, when the composition is irradiated with microwaves, its rapid and uniform polymerization starts to occur from its inside, resulting in the achievement of effective polymerization.

The reasons why the composition according to the present invention can so effectively be polymerized by microwaves are considered to reside in the following. When microwaves are applied to the composition, the reaction of the barbituric acid derivative with the quaternary ammonium chloride is markedly promoted to allow rapid generation of radicals, and the polymerization reaction starts to occur rapidly from within the composition owing to the fact that the molecular motion of the composition per se is excited. At the same time, the polymerization begins to occur from the outside of the composition, since the organic peroxide contained in the composition decomposes rapidly on account of indirect heating from the plaster heated rapidly by microwaves to generate radicals. In consequence, the polymerization starts to occur simultaneously through the whole composition from both outside and inside thereof to assure its uniform polymerization. It is to be noted that the cross-linking agent is effective as a promotor for the polymerization reaction rate, which can finish the polymerization by short-time microwave irradiation and, through its cross-linking effect, affords an intimate and homogenous structure to the resulting set product and limit the deformation thereof caused as by water absorption. For that reason, in the case where the composition according to the present invention is polymerized by the microwave curing method, a homogeneous set product can be obtained by short-time irradiation of microwaves regardless of variations in the thickness of the composition per se and the thickness of the plaster layer surrounding it, as viewed from the standpoint of the form of dentures. Any porosity is not found in the set product owing to the absence of concentrated contraction resulting from uneven starting of the polymerization. Furthermore, uniform polymerization of the composition as a whole appears to make a contribution to limiting internal strain. These make it possible to prepare dentures of highly improved fitting accuracy.

It has been known for long that the barbituric acid derivatives used in the present invention are promotors for polymerizable monomers such as methacylate esters. Proposals have also been made of systems for initiating polymerization without heating but within a short time, which comprise a combination of the barbituric acid derivatives with halogens and heavy metal compounds. However, in the purpose of the present invention, sole use of the barbituric acid derivatives is not effective at all. Nor does the combination thereof with halogens and heavy metal compounds render it possible to fill and pressurize a dough-form product of the powdery and liquid components in a denture negative model, since the polymerization reaction then starts at a much more premature stage. In the present invention, the barbituric acid derivative is used in combination with the organic peroxide and quaternary ammonium chloride. It is essentially required, however, that, at the time when they are mixed with other constituents into a composition, its polymerization is not started at all at room temperature, or its polymerization is postponed till the lapse of a sufficiently long time, even though it is capable of beginning its polymerization at room temperature, and its polymerization can be initiated rapidly upon irradiation with microwaves. For the reasons as mentioned just above, certain limitations are imposed upon the type and amount of the barbituric acid derivative, organic peroxide and quaternary ammonium chloride and the amount of the cross-linking agent to be used in the present invention.

DETAILED DESCRIPTION OF THE PRESENT INVENTION

The present invention will now be explained in further detail. In the present invention, the methacrylate ester polymer used as the main constituent of the powdery component is required to have a mean particle size of 50 to 120 microns. When using a methacrylate ester polymer of less than 50 microns, since the powdery component shows unsatisfactory compatibility with respect to the liquid component at the time of mixing, it is difficult to obtain a uniform mixed product which, after polymerization, provides a homogeneous set product. Since the surface area of powder is increased, it is also necessary to increase the amount of the liquid component required for mixing. However, this results in an increase in contraction during polymerization, which is also responsible for occurence of porosity or deformation. When using a methacrylate ester polymer of higher than 120 microns in the mean particle size, it is difficult to uniformly disperse and stably maintain the required amounts of the barbituric acid derivative and organic peroxide in the powdery polymer. At the same time, when mixed with the liquid component, it is difficult for the monomer to sufficiently permeate into the polymer. This gives an inhomogeneous dough-form resin, which gives rise to internal porosity at the time of polymerization, or provides an inhomogeneous set product.

The methacrylate ester polymer used includes a methacrylate ester polymer and a copolymer composed mainly of methyl methacrylate represented by methyl methacrylate.ethyl methacrylate copolymers, methyl methacrylate.butyl methacrylate copolymers, methyl methacrylate.trimethylolpropane trimethacrylate copolymers and methyl methacrylate.styrene copolymers, for instance. The methyl methacrylate polymer may be used in admixture with these copolymers.

In order to regulate the time for reach the resin mixture dough stage or the workability of the dough-form resin, the methyl methacrylate polymer, the copolymer composed mainly of a methyl methacrylate polymer or the mixture consisting of methyl methacylate polymer and a copolymer composed mainly of methyl methacylate and added thereto may be mixed with one or more methacrylate ester polymers other than methyl methacrylate and/or one or more copolymers of methacrylate esters other than methyl methacrylate. The methacrylate ester polymers other than methyl methacrylate include, e.g., ethyl methacrylate polymer and butyl methacrylate polymer, whereas the copolymers of methacrylate esters other than methyl methacrylate include, e.g., ethyl methacrylate.butyl methacrylate copolymers and ethyl methacrylate. trimethylolpropane trimethacrylate copolymers. However, in order to achieve the features of the present invention in a more effective manner, up to 25 weight parts of the methacrylate ester polymers other than methyl methacrylate or the copolymers of methacrylate esters other than methyl methacrylate may preferably be mixed with the methyl methacrylate polymer, the copolymer composed mainly of methyl methacrylate or the mixture obtained by adding the copolymer composed mainly of methyl methacrylate to the methyl methacrylate polymer.

The barbituric acid derivative to be incorporated into the powdery component is preferably one having an alkyl or aryl substituent at the 5 position. Mentioned to this end are, for instance, 1,3,5-trimethylbarbituric acid, 1,3-dimethyl-5-phenylbarbituric acid, 1,3-dimethyl-5-isobutylbarbituric acid, 5-ethylbarbituric acid, 5-n-butylbarbituric acid, 5-phenylbarbituric acid, 1-benzyl-5-phenylbarbituric acid and 1-cyclohexyl-5-ethylbarbituric acid. Particular preference is given to 1-benzyl-5-phenylbarbituric acid, 5-n-butylbarbituric acid and 1-cyclohexyl-5-ethylbarbituric acid. These acid derivatives may be used alone or in admixture. It is preferred that these barbituric acid derivatives are added in an amount of 0.05 to 1 weight part per 100 weight parts of the methacrylate ester polymer. In an amount of below 0.05 weight parts, their promoting effect upon the polymerization reaction, which occurs when microwaves are applied to the composition, is so insufficient that the resulting set product is inhomogeneous and contain internal porosity. In an amount exceeding 1 weight part, on the other hand, the polymerization reaction, which occurs when mixed with the liquid component containing the quaternary ammonium chloride, is initiated at too premature stage to make sure of a suitable manipulation time, and the resulting set product tends to deteriorate in respect of water resistance.

The organic peroxide to be incorporated in the powdery component include, e.g., benzoyl peroxide, 4,4'-dichlorobenzoyl peroxide, 2,4-dichlorobenzoyl peroxide and dilauroyl peroxide. Particular preference is given to benzoyl peroxide and dilauroyl peroxide. These peroxides may be used alone or in combination.

Preferably, these organic peroxides are used in an amount of 0.1 to 2 weight parts per 100 weight parts of the methacrylate ester polymer. In an amount of below 0.1 weight part, their capability of rapidly promoting the polymerization of the overall composition in a chain reactional manner becomes insufficient after that polymerization is initiated by microwave irradiation. In consequence, the resulting set product is obtained in an inhomogeneous state. In an amount exceeding 2 weight parts, on the contrary, the amount of heat generated during the polymerization reaction is increased with a remarkable rise in the internal temperature of the compositions, which in turn causes vaporization of the methyl methacrylate monomer and, hence, occurrence of porosity.

In order to reproduce a gingival color, coloring pigments based on organics or inorganics or colored fibers may further be added to the powdery component.

The monomethacrylate ester monomer used for the liquid component in the present invention is mainly a methyl methacrylate monomer. In order to regulate the time for reach its mixture with the powdery component dough stage and the workability of the dough-form resin, it may be mixed with monomethacrylate ester monomers other than the methyl methacrylate monomer.

Other monomethacrylate ester monomers to be used include, e.g., ethyl methacrylate monomer, butyl methacrylate monomer, isobutyl methacrylate monomer, methacrylic acid 2-ethylhexyl monomer, methacrylic acid cyclohexyl monomer and methacrylic acid tetrahydrofurfuryl monomer. These may be used alone or in admixture. In order to achieve the features of the present invention in a more effective manner, however, they are preferably mixed in an amount of up to 25 weight parts with 100 weight parts of the methyl methacrylate monomer.

The cross-linking agent to be incorporated into the liquid component according to the present invention includes, e.g., polyfunctional methacrylates and diallyl phthalates or mixtures thereof. Mentioned for the polyfunctional methacrylates are ethylene glycol dimethacrylate, 1,3-butanediol dimethacrylate, 1,4-butanediol dimethacrylate and trimetylolpropane trimethacrylate, for instance. These may be used alone or in combination, and are preferably added in an amount of 0.1 to 15 weight parts per 100 weight parts of the monomethacrylate ester monomer. In an amount of below 0.1 weight part, the polymerization reaction rate is so insufficient that the resulting set product tends to be inhomogeneous, and has too a low cross-linked density to obtian an intimate structure and, hence, is readily deformable. On the other hand, an amount exceeding 15 weight parts results in an increase in the contraction by polymerization with a lowering of the fitting accuracy of dentures, and provides a set product which is fragile and breakable.

It is preferred that the quaternary ammonium chloride to be incorporated into the liquid component according to the present invention is easily soluble in the methacrylate ester monomer. Mentioned to this end are, e.g., dodecyltrimethylammonium chloride, lauryldimethylbenzylammonium chloride, coconut alkyldimethylbenzylammonium chloride, dilauryldimethylammonium chloride and dioctyldimethylammonium chloride. Particular preference is given to lauryldimethylgenzylammonium chloride, dilauryldimethylammonium chlorde and dioctyldimethylammonium chloride. These quaternary ammonium chlorides may be used alone or in admixture, and are preferably added in an amount of 0.05 to 1 weight parts relative to 100 weight parts of the monomethylacrylate ester monomer. In an amount of less than 0.05 weight parts, the generation of radicals due to its reaction with the barbituric acid derivative is so insufficient that its promoting effect upon the polymerization reaction by microwave irradiation is insufficient, thus giving an inhomogeneous set product containing internal porosity. An amount exceeding 1 weight part starts the polymerization reaction at too premature stage to ensure a suitable manipulation time, and provides a set product which tends to deteriorate in respect of water resistance.

For storage stability, the liquid component may optionally contain a polymerization inhibitor represented by, e.g., hydroquinone, hydroquinone monomethyl ether, 2-hydroxy-4-methoxybenzophenone, 2,4-dimethyl-6-tert.-butyl phenol and butylhydroxytoluene.

EXAMPLES

In the following Examples and Comparative Examples, Experiments 1 to 6 were carried out with the following compositions prepared therefor to confirm the effect of the present invention. It is to be understood, however, that the invention is not limited thereto.

EXAMPLES 1 to 20

The compositions are set forth in Table 1.

Comparative Example 1

Commercially available heat-curing base resin (GC Dental Industrial Corp., available under the trade name of Acron).

Comparative Examples 2 to 12

The compositions are set forth in Table 2. In what follows, however, Comparative Examples 2 to 12 will be explained in further detail.

In Comparative Example 2, a typical composition of the ordinary heat-curing base resin was prepared. In Comparative Examples 3 and 4, use was made of the compositions which correspond to those in Ex. 1, but in which the average particle size of each methyl methacrylate polymer departed from the range of 50 to 120 microns. In Comparative Examples 5 and 6, the amount of each barbituric acid derivative added departed from the range of 0.05 to 1.0 weight part. In Comparative Examples 7 and 8, the amount of each quaternary ammonium chloride added departed from the range of 0.05 to 1.0 weight part. In Comparative Examples 9 and 10, use was made of the compositions which correspond to those in Example 4, but in which the amount of each organic peroxide added departed from the range of 0.1 to 2 weight parts. In Comparative Examples 11 and 12, use was made of the compositions which corresponded to those in Ex. 9, but in which the amount of each cross-linking agent added departed from the range of 0.1 to 15 weight parts.

TABLE 1

| | | Example 1 | Example 2 | Example 3 | Example 4 | Example 5 | Example 6 | Example 7 | Example 8 | Example 9 | Example 10 | Example 11 | Example 12 | Example 13 | Example 14 | Example 15 | Example 16 | Example 17 | Example 18 | Example 19 | Example 20 |
|---|---|---|---|---|---|---|---|---|---|---|---|---|---|---|---|---|---|---|---|---|---|
| Powdery Component | | | | | | | | | | | | | | | | | | | | | |
| Methyl methacrylate polymer (mean particle size 100 μm) | (weight parts) | 100 | 100 | 50 | 50 | — | — | 100 | — | 50 | 50 | — | 50 | 100 | 85 | — | 100 | — | — | — | — |
| Methyl methacrylate polymer (mean particle size 60 μm) | (weight parts) | — | — | 50 | 50 | 100 | 100 | — | 100 | 50 | 50 | 100 | 50 | — | — | 85 | — | 100 | 100 | 100 | — |
| Ethyl methacrylate polymer (mean particle size 80 μm) | (weight parts) | — | — | — | — | — | — | — | — | — | — | — | — | — | 15 | 15 | — | — | — | — | — |
| Methyl methacrylate copolymer Ethyl methacrylate (mean particle size 90 μm) | (weight parts) | — | — | — | — | — | — | — | — | — | — | — | — | — | — | — | — | — | — | — | 100 |
| 5-n-butylbarbituric acid | (weight parts) | — | — | — | — | 0.8 | 0.5 | 0.1 | 0.3 | — | — | 0.3 | — | — | — | 0.6 | — | 0.5 | 0.1 | — | 0.5 |
| 1-benzyl-5-phenylbarbituric acid | (weight parts) | 0.2 | 0.15 | — | — | — | — | 0.2 | — | 0.1 | 0.2 | 0.1 | 0.1 | 0.2 | 0.3 | — | 0.1 | — | — | 0.3 | — |
| 1-cyclohexyl-5-ethylbarbitric acid | (weight parts) | — | — | 0.5 | 0.5 | — | — | — | 0.2 | 0.2 | 0.1 | 0.2 | 0.1 | — | — | — | — | — | 0.4 | — | — |
| Benzoyl peroxide | (weight parts) | 1.0 | 1.0 | 0.5 | — | 0.5 | 1.0 | 0.5 | — | 1.0 | 0.5 | 0.2 | 1.0 | 1.0 | 0.5 | 1.0 | 1.0 | 1.0 | 0.5 | 0.5 | 1.0 |
| Dilauroyl Peroxide | (weight parts) | — | — | — | 1.5 | — | — | — | 0.3 | — | — | — | — | 0.5 | — | — | 0.3 | — | — | — | — |
| Liquid Component | | | | | | | | | | | | | | | | | | | | | |
| Methyl methacrylate monomer | (weight parts) | 100 | 100 | 100 | 100 | 100 | 100 | 100 | 100 | 100 | 100 | 100 | 100 | 100 | 100 | 100 | 100 | 100 | 100 | 85 | 100 |
| Methacrylic acid 2-ethylhexyl monomer | (weight parts) | — | — | — | — | — | — | — | — | — | — | — | — | — | — | — | — | — | — | 15 | — |
| Ethylene glycol dimethacrylate | (weight parts) | 5 | — | 5 | — | 3 | 5 | 3 | 3 | 5 | 3 | — | 5 | 5 | 3 | 3 | — | 5 | — | 5 | 10 |
| 1,3-butanediol dimethacrylate | (weight parts) | — | 7 | 5 | — | — | — | — | — | — | — | 0.5 | — | 3 | 3 | 3 | 7 | — | 3 | — | — |
| Dially phthalate | (weight parts) | — | — | — | 10 | — | — | — | — | — | — | — | — | — | 10 | 5 | — | — | — | — | — |
| Dilauryl dimethylammonium chloride | (weight parts) | 0.4 | — | 0.8 | — | 0.2 | — | 0.3 | — | 0.3 | 0.3 | — | 0.3 | 0.4 | 0.3 | — | 0.2 | 0.2 | 0.1 | 0.3 | — |
| Lauryl dimethyl benzylammonium chloride | (weight parts) | — | 0.3 | — | 0.7 | — | — | — | — | — | — | 0.1 | 0.1 | — | — | — | 0.2 | — | 0.1 | — | — |
| Dioctyl dimethylammonium chloride | (weight parts) | — | — | — | — | — | 0.5 | — | 0.5 | — | — | — | — | — | — | 0.5 | — | 0.4 | 0.3 | — | 0.5 |
| 2,4-dimethyl-6-tert-butylphenol* | (weight parts) | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 |

*Polymerization inhibitor

TABLE 2

| Powder/Component | | Comparative Example 2 | Comparative Example 3 | Comparative Example 4 | Comparative Example 5 | Comparative Example 6 | Comparative Example 7 | Comparative Example 8 | Comparative Example 9 | Comparative Example 10 | Comparative Example 11 | Comparative Example 12 |
|---|---|---|---|---|---|---|---|---|---|---|---|---|
| Methyl methacrylate polymer (mean particle size 30 μm) | (weight parts) | — | 100 | — | — | — | — | — | — | — | — | — |
| Methyl methacrylate polymer (mean particle size 60 μm) | (weight parts) | — | — | — | 100 | 100 | 100 | 100 | 50 | 50 | 50 | 50 |
| Methyl methacrylate polymer (mean particle size 100 μm) | (weight parts) | 100 | — | — | — | — | — | — | 50 | 50 | 50 | 50 |
| Methyl methacrylate polymer (mean particle size 140 μm) | (weight parts) | — | — | 100 | — | — | — | — | — | — | — | — |
| 5-n-butylbarbituric acid | (weight parts) | — | — | — | 0.03 | 1.2 | 0.8 | 0.2 | — | — | — | — |
| 1-benzyl-5-phenylbarbituric acid | (weight parts) | — | 0.2 | 0.2 | — | — | — | — | — | — | 0.1 | 0.1 |
| 1-cyclohexyl-5-ethylbarbituric acid | (weight parts) | — | — | — | — | — | — | — | 0.5 | 0.5 | 0.2 | 0.2 |
| Benzoyl peroxide | (weight parts) | 0.5 | 1.0 | 1.0 | 0.5 | 0.5 | 0.5 | 0.5 | — | — | 1.0 | 1.0 |
| Dilauroyl peroxide | (weight parts) | — | — | — | — | — | — | — | 0.05 | 2.5 | — | — |
| Liquid Component | | | | | | | | | | | | |
| Methyl methacrylate monomer | (weight parts) | 100 | 100 | 100 | 100 | 100 | 100 | 100 | 100 | 100 | 100 | 100 |
| Ethylene glycol dimethacrylate | (weight parts) | 3 | 5 | 5 | 3 | 3 | 3 | — | — | — | 0.02 | 30 |
| 1,3-butanediol dimethacrylate | (weight parts) | — | — | — | — | — | — | 3 | — | — | — | — |
| Diallyl phthalate | (weight parts) | — | — | — | — | — | — | — | — | 10 | — | — |
| Dilauryl dimethylammonium chloride | (weight parts) | — | 0.4 | 0.4 | 0.8 | 0.2 | 0.03 | 1.2 | — | — | 0.3 | 0.3 |
| Lauryl dimethyl benzylammonium chloride | (weight parts) | — | — | — | — | — | — | — | 0.7 | 0.7 | — | — |
| 2,4-dimethyl-6-tert brtylphenol* | (weight parts) | 0.01 | 0.01 | 0.01 | 0.01 | 0.01 | 0.01 | 0.01 | 0.01 | 0.01 | 0.01 | 0.01 |

*Polymerization inhibitor

Experiment 1

With the compositions of Ex. 1 and Comparative Examples 1 and 2, the following experiments were carried out to investigate the polymerization properties thereof, when irradiated with microwaves.

Experimental Procedures

In each experimental run, a plaster negative model of a rectangular parallelepiped of 20 x 15 x 3 mm was placed and prepared at the center of the FRP flask. Each composition was mixed together in a powder to liquid component ratio of 100 g to 43 ml to form a doughlike product which was filled and pressurized in the negative model, and the flask was placed in an microwave oven wherein it was irradiated with microwaves for polymerization. The polymerization was effected in varied periods of irradiation time. Immediately upon the completion of microwave irradiation, the flask was put into cold water and held therein for 30 minutes. Thereafter, the polymerized sample under test was removed and allowed to stand at room temperature for 24 hours to measure the Knoop hardness. To this end, the Knoop hardness of the sample was measured at five points on the front side (to which microwaves were applied) and at five points on the rear side (the opposite side), and the relationship between the average value of ten mesurements and the microwave-irradiation time. In all the experimental runs, the frequency of microwaves applied was 2450 MHz at an high-frequency output of 500 W. The results are shown in FIG. 1 wherein Curves I, II and III correspond to Ex. 1, Comparative Example 1 (Acron) and Comparative Example 2, respectively.

Experiment 2

Using the compositions of Ex. 2 and Comparative Example 1, actual dentures were polymerized and prepared by the microwave curing method and, thereafter, were cut off to study the internal porosity contained therein. In each experimental run, the polymerization was carried out by applying microwaves to the compositions for 3 minutes at an output of 500 W. The results are set forth in FIG. 2 (Ex. 2) and FIG. 3 (Comparative Example 1).

Figure 1:
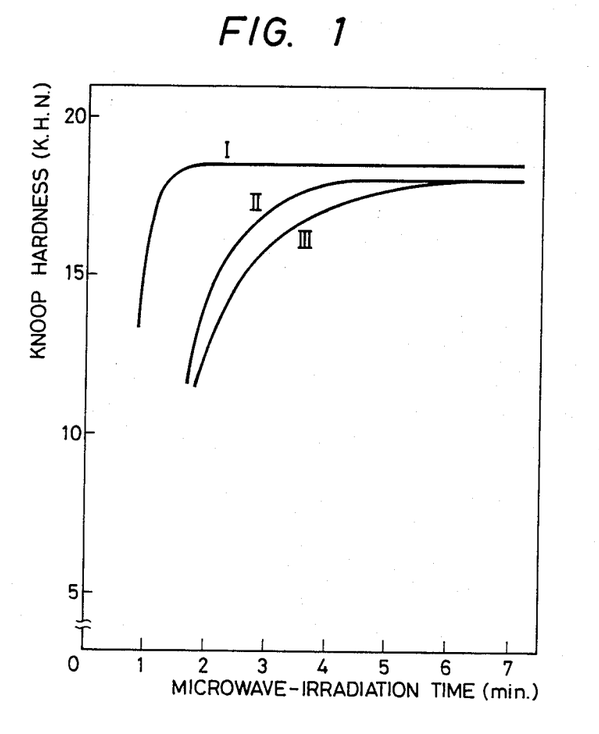
FIG. 1 shows a view illustrating the relationship between the irradiation time of microwaves and the Knoop hardness of the cured products obtained from the compositions of Example 1 and Comparative Examples 1 and 2, when polymerized by irradiation of microwaves.

From FIG. 1, it is found that the polymerization of the composition of Ex. 1 is completed to give a stable hardness by only 2 to 3 minute-microwave irradiation, whereas 5 to 6 minutes or longer periods of time are required by the time the compositions of Comparative Examples 1 and 2 are polymerized into a stable hardness. It is to be appreciated that 5-minute or longer microwave irradiation should be avoided, since it causes an excessive increase in the internal temperature of the flask, which in turn leads to thermal deformation of the cured resin and rapid deterioration of the FRP flask. In this regard, the compositions of Comparative Examples 1 and 2 offer problems in view of practical use.

Figure 2:
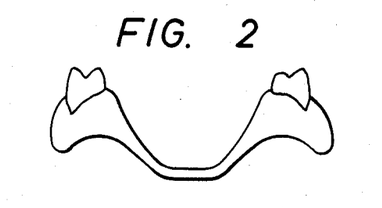
FIG. 2 is a sectional view illustrating one actual denture obtained by polymerizing the composition of Example 2 by irradiation of microwaves.
Figure 3:
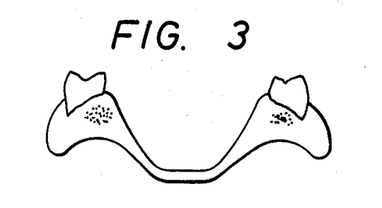
FIG. 3 is a sectional view illustrating one actual denture obtained by polymerizing the composition of Comparative Example 1 by irradiation of microwaves.

From FIGS. 2 and 3 showing the results of the actual dentures polymerized by the microwave curing method, it is also found that no internal porosity is observed in the denture obtained from the composition of Ex. 1, whereas much porosity are present in the interior of the resin of the alveolar portion, below the artificial teeth, of the denture formed of the composition of Comparative Example 1.

From the aforesaid results, it is noted that when polymerized by microwaves, the ordinary heat curing base resin offers the problems that it provides a set product which is inhomogeneous due to the presence of unpolymerized matters, or contains internal porosity, and are thus unsuitable for use with the microwave curing method. However, they indicate that such problems can be solved by the compositions of the present invention.

Next, Experiments 3 to 6 were carried out with all the compositions of Examples 1 to 20 and Comparative Examples 1 to 12. The results are summarized in Table 3.

The general procedures and object of each experiment are as follows.

Experiment 3

Each sheet-like sample was polymerized, and its Knoop hardness was measured at a plurality of varied positions. The mean value of the measurements and the standard deviation value were found to determine the homogeneity of the set product of each composition from the magnitude of a difference therebetween.

Experiment 4

Each sample having a certain thickness was polymerized to observe the internal porosity contained therein, whereby study was made of the possibility of occurence of porosity, when each composition was polymerized.

Imposed upon the size of each sample were severer conditions than those applied upon the ordinary denture under which porosity were found to occur. The samples showing no sign of any porosity in this experiment would never give rise to any porosity therein, even when used for ordinary dentures.

Experiment 5

Each of relatively thin samples having a metal embedded therein was polymerized to observed the presence of porosity in the resin portion around the metal, whereby study was made of the possibility of occurrence of porosity contributable to the metal which polymerizing the denture containing therein clasps and bars.

Experiment 6

Each sample was polymerized into the form accommodative to an angular stone cast, and was placed under certain conditions. Thereafter, the sample was fitted into the original stone cast to determine the discrepancy between the sample and the original stone cast, whereby study was made of the fitting accuracy of the set product obtained from each composition.

In what follows, the procedures of each experiment will be explained in further detail.

Details of the Experimental Procedures

In the following experiments, each of the compositions of Examples 1 to 20 and Comparative Examples 1, 2 and 4-12 was mixed together in a powder to liquid component ratio of 100 g to 43 ml for use. However, the composition of Comparative Example 3 was mixed together in a powder to liquid component ratio of 100 g to 50 ml, since it could not be mixed in the aforesaid ratio due to its small mean particle size. All the samples were polymerized by placing the respective flasks in an microwave oven for domestic use, wherein they were irradiated with microwaves at an output of 500 W for 3 minutes.

Experiment 3

Figure 4:
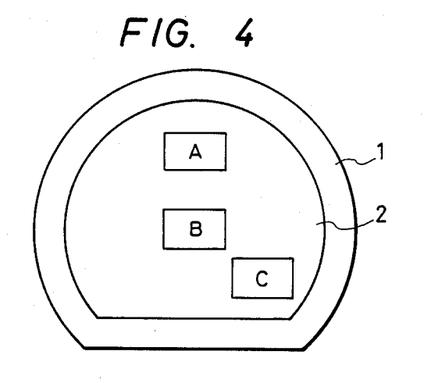
FIG. 4 is a view showing an arrangement of a negative model in the FRP flask.
Figure 5:
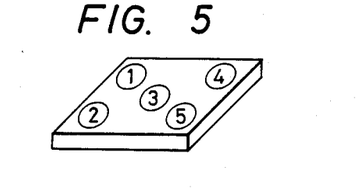
FIG. 5 is a view showing the positions at which the Knoop hardness of one sample is measured.

Three plaster negative models each of a rectangular parallelepiped of 20×15×3 mm were placed and prepared at positions A, B and C in FIG. 4, in plaster using the FRP flask. A dough-form powdery and liquid-component product having the respective compositions was filled and pressurized in the negative models for polymerization. In FIG. 4, reference numeral 1 stands for the FRP flask, and 2 indicates plaster. After the polymerization, the flask was put into cold water for 30-minute cooling, following which the polymerized samples were removed therefrom and allowed to stand at room temperature for 24 hours to measure their Knoop hardness. More exactly, the Knoop hardness of one sample was measured at five positions (1) to (5) in FIG. 5 on both sides using three test samples. In this manner, the samples obtained from one composition were measured in respect of their Knoop hardness at a total of 30 positions to calculate the mean value and standard deviation value.

Experiment 4

A plaster negative model of a rectangular parallelepiped of 30×30×15 mm was positioned and prepared at the center of the FRP flask. A dough-form made by way of mixing powdery and liquid-component product having the respective compositions was filled and pressurized in the negative model for polymerization. After the polymerization, the flask was put into cold water for 30-minute cooling, following which the polymerized sample was removed. The sample obtained from each composition was cut off at its center to observe the internal porosity contained therein.

Experiment 5

Figure 6:
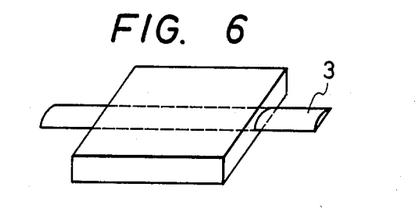
FIG. 6 is a schematical view showing one sample.

Using the FRP flask, a plaster negative model of a rectangular prallelepiped of 20 x 15 x 4 mm was prepared, which was fixedly provided through its center with a Co-Cr lingual bar of 3 mm in width and 1.2 mm in thickness. A dough-form made by way of mixing powdery and liquid-component product having the respective compositions was filled and pressurized in the negative model for polymerization. After the polymerization, the flask was put into cold water for 30-minute cooling, following which the polymerized sample was removed therefrom. The sample obtained from each composition, as shown in FIG. 6, was cut off at its center to observe the internal porosity contained therein. In FIG. 6, reference numeral 3 stands for the lingual bar.

Experiment 6

Figure 7:
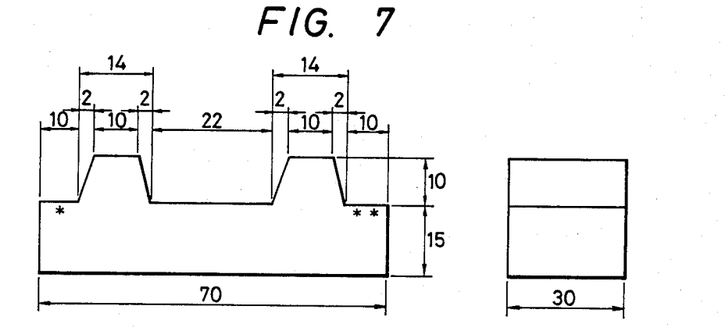
FIG. 7 is front and side views showing one angular stone cast with its size.

An angular stone cast, the size of which is shown in mm in FIG. 7, was prepared with dental super-hard plaster (GC Dental Industrial Corp.; available under the trade name of Fujirock), and paraffin wax of 1.5 mm in thickness and 30 mm in width was brought into pressure contact with a plaster face portion, marked * - ** in FIG. 7, to form a wax pattern accommodative to the angular stone cast. In the conventional manner, the wax pattern was invested together with the stone cast in investing plaster placed in the FRP flask. After the plaster had been set, the wax was removed to obtain a negative model in which a dough-form made by way of mixing powdery and liquid-component product having the respective compositions was filled and pressurized for polymerization.

Figure 8:
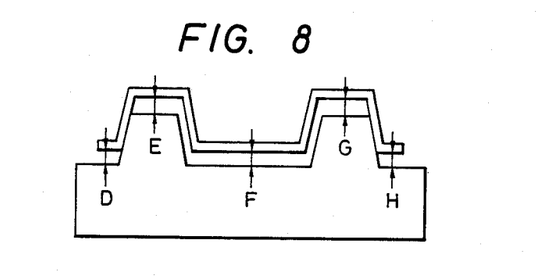
FIG. 8 is a view illustrating the manner for measuring the discrepancy between one sample and the angular stone cast.

After the polymerization, the flask was put into cold water for 30-minutes cooling, following which the polymerized sample was removed together with the model therefrom. The sample was then taken out of the stone cast, and was immersed into distilled water of 37° C. for seven days. After the sample obtained from each composition had been immersed into distilled water for seven days, it was re-fitted onto the original angular stone cast to determine the discrepancy between the sample and the original stone cast, as shown in FIG. 8. Table 3 shows the mean value of two measurements at positions D and H, the mean value of two measurements at positions E and G and one measurement at a position F.

TABLE 3

|  | Experiment 3 Knoop Hardness (HK) | | Experiment 4 Porosity | Experiment 5 | Experiment 6 Discrepancy (mm) | | |
|---|---|---|---|---|---|---|---|
|  | Mean Value | Standard Deviation Value | Sample of Certain Thickness | Metal-Embedded Sample | DH | EG | F |
| Example 1 | 18.4 | 0.3 | O | O | 0.06 | 0.01 | 0.07 |
| Example 2 | 18.4 | 0.3 | O | O | 0.07 | 0.01 | 0.07 |
| Example 3 | 18.1 | 0.4 | O | O | 0.07 | 0.01 | 0.06 |
| Example 4 | 18.4 | 0.3 | O | O | 0.08 | 0.01 | 0.04 |
| Example 5 | 18.1 | 0.3 | O | O | 0.06 | 0.01 | 0.06 |
| Example 6 | 18.2 | 0.4 | O | O | 0.08 | 0.01 | 0.05 |
| Example 7 | 18.4 | 0.2 | O | O | 0.05 | 0.00 | 0.06 |
| Example 8 | 18.3 | 0.2 | O | O | 0.05 | 0.00 | 0.04 |
| Example 9 | 18.4 | 0.2 | O | O | 0.04 | 0.00 | 0.04 |
| Example 10 | 18.4 | 0.2 | O | O | 0.04 | 0.00 | 0.04 |
| Example 11 | 17.9 | 0.2 | O | O | 0.05 | 0.00 | 0.06 |
| Example 12 | 18.4 | 0.2 | O | O | 0.04 | 0.00 | 0.05 |
| Example 13 | 18.4 | 0.2 | O | O | 0.05 | 0.00 | 0.06 |
| Example 14 | 17.8 | 0.5 | O | O | 0.08 | 0.02 | 0.07 |
| Example 15 | 17.6 | 0.4 | O | O | 0.06 | 0.02 | 0.07 |
| Example 16 | 18.0 | 0.3 | O | O | 0.06 | 0.01 | 0.05 |
| Example 17 | 18.4 | 0.2 | O | O | 0.05 | 0.00 | 0.04 |
| Example 18 | 18.3 | 0.2 | O | O | 0.04 | 0.00 | 0.03 |
| Example 19 | 17.9 | 0.4 | O | O | 0.06 | 0.01 | 0.07 |
| Example 20 | 17.5 | 0.4 | O | O | 0.08 | 0.02 | 0.08 |
| Comparative Example 1 | 16.2 | 2.0 | XX | X | 0.27 | 0.28 | 0.30 |
| Comparative Example 2 | 15.8 | 2.2 | XX | X | 0.37 | 0.33 | 0.38 |
| Comparative Example 3 | 17.2 | 1.2 | XX | X | 0.24 | 0.20 | 0.26 |
| Comparative |  |  |  |  |  |  |  |

TABLE 3-continued

|  | Experiment 3 Knoop Hardness (HK) | | Experiment 4 Porosity | Experiment 5 | Experiment 6 Discrepancy (mm) | | |
| --- | --- | --- | --- | --- | --- | --- | --- |
|  | Mean Value | Standard Deviation Value | Sample of Certain Thickness | Metal-Embedded Sample | DH | EG | F |
| Example 4 | 15.8 | 3.0 | XX | X | 0.18 | 0.10 | 0.11 |
| Comparative Example 5 | 16.1 | 2.3 | XX | X | 0.28 | 0.30 | 0.29 |
| Comparative Example 6* | — | — | — | — | — | — | — |
| Comparative Example 7 | 16.3 | 2.2 | XX | X | 0.26 | 0.28 | 0.28 |
| Comparative Example 8* | — | — | — | — | — | — | — |
| Comparative Example 9 | 17.2 | 1.3 | X | Δ | 0.20 | 0.09 | 0.12 |
| Comparative Example 10 | 18.1 | 0.6 | XX | XX | 0.08 | 0.01 | 0.06 |
| Comparative Example 11 | 17.1 | 0.9 | Δ | O | 0.18 | 0.16 | 0.20 |
| Comparative Example 12 | 18.5 | 0.3 | O | O | 0.34 | 0.31 | 0.42 |

*The compositions of Comparative Examples 6 and 8 could not be put under experiment since they were set at the step of dough-forming.
O: No porosity found
Δ: Little porosity found
X: Much porosity found
XX: Much porosity found with voids (assembly of porosity)

From the results of Table 3, it has been found that, when polymerized by 3-minute irradiation of microwaves at an output of 500 W, all the compositions of Examples 1 to 20 provide cured products which show stable harndess as evident from limited or reduced variations in Knoop hardness, and are homogeneous. It has also been found that, even when the samples having a certain thickness and having a metal embedded therein are polymerized, the resulting products show no sign of any internal porosity. From the results of testing wherein those products were immersed in water of 37° C. for one week, it has further been found that they undergo very limited deformation, and are thus of excellent fitting accuracy.

However, it has been noted that the cured products obtained from the ordinary heat-curing base resin and the typical composition prepared therefrom, illustrated in Comparative Examples 1 and 2, are inhomogeneous as expressed in terms of large variations in Knoop hardness, contain therein internal porosity, and are of unsatisfactory fitting accuracy.

From the results of Comparative Examples 3 to 12, it is clearly understood that the effect of the present invention is not sufficiently achievable, when the mean particle size of the methacrylate ester polymer and any one of the amounts of the barbituric acid derivative, organic peroxide, quaternary ammonium chloride and cross-linking agent departs from the recommendable ranges as defined in the appended claims.

Additionally speaking, the respective components in Comparative Examples 3 and 4 were added in the same amounts as in Example 1, provided however that the mean particle size of the methacrylate ester polymer departed from the recommendable range. It has been found that the cured product obtained in Comparative Example 3 wherein the polymer used has a mean particle size lower than the lower limit of the preferable range shows a somewhat large variation in hardness, contains internal porosity, and is of unsatisfactory fitting accuracy due to its large contraction caused by use of a large amount of liquid. It has also been found that the cured product obtained in Comparative Example 4 wherein the polymer used has a mean particle size exceeding the upper limit of the preferable range shows a large variation in hardness, contains internal porosity, and is of somewhat unsatisfactory fitting accuracy.

In Comparative Examples 5 to 8, the amount of the barbituric acid derivative or the quaternary ammonium chloride departed from the preferred range. Referring to the compositions of Comparative Examples 6 and 8 wherein the amount of the barbituric acid derivative or the quaternary ammonium chloride exceeded the upper limit of the preferable range, the mixture of the powdery and liquid components started to be polymerized at a premature stage, and thus could not be used, because there was no sufficient time for manipulation. Referring also to the compositions of Comparative Examples 5 and 7 wherein the amounts of the respective additives were lower than the lower limit of the preferred ranges, the resulting cured products showed a large variation in hardness, contained internal porosity, and were of unsatisfactory fitting accuracy.

The compositions of Comparative Examples 9 and 10 corresponded to that of Example 4, but contained the organic peroxides in an amount departing from the preferred range. Referring to the composition of Comparative Example 9 wherein the amount of the organic peroxide was lower than the lower limit of the preferred range, the resulting cured product showed a somewhat large variation in hardness, contained some internal porosity, and were of somewhat unsatisfactory fitting accuracy. Referring on the other hand to the composition of Comparative Example 10 wherein the amount of the peroxide exceeded the upper limit of the preferred range, the resulting cured product showed a small variation in hardness and was of well fitting accuracy, but was found to contain a remarkable number of internal porosity areas.

The compositions of Comparative Examples 11 and 12 corresponded to that of Example 9, but included the cross-linking agents in an amount departing from the preferred range. Referring to the composition of Comparative Example 11 wherein the amount of the cross-linking agent was lower than the lower limit of the preferred range, the resulting cured product showed a small variation in hardness and was found to contain a slight internal porosity, but was of somewhat unsatisfactory fitting accuracy. Referring on the other hand to the composition of Comparative Example 12 wherein the amount of the crosslinking agent exceeded the upper limit of the preferred range, the resulting cured product showed a small variation in hardness and was freed from any internal porosity, but showed large contraction and was thus of unsatisfactory fitting accuracy.

The foregoing Experiments 3 to 6 were carried out with the specific samples, but under the conditions severer than those for the polymerization of actual dentures in clinical applications. Hence, the compositions showing satisfactory results in these experiments would bring about more successful results, when used for actual dentures.

Accordingly, when the compositions of Examples 1 to 20 according to the present invention are treated by the microwave curing method for the polymerization of dentures, they provide sufficiently homogeneous cured products by only 3-minute irradiation of microwaves. Even when a denture having a certain thickness or including a metal is polymerized, it is possible to prepare a denture having no internal porosity and of excellent fitting accuracy.

A polymerization time of 90 to 120 minutes was required for the polymerization of the ordinary heat-curing base resin by the conventional heat-curing method. With the resinous compositions for denture base according to the present invention, however, it is possible to polymerize dentures by only several-minute irradiation of microwaves, if the microwave curing method is applied. In the case where the polymerization of dentures is carried out by the microwave curing method, using the resinous compositions for denture base according to the present invention, it is possible to solve all the problems arising when the polymerization of dentures is effected by the microwave curing method, using the ordinary heat-curing base resin. In other words:

(1) Since the polymerization proceeds sufficiently by only several-minute irradiation of microwaves, there are obtained cured products which are free from any unpolymerized matters and homogeneous.

(2) Any porosity is not found in the interior of the resin of a thicker portion of a denture.

(3) Even when a denture including a clasp or a bar or a metal-plated denture is polymerized, any porosity is not found in the resin around the metal.

(4) Due to its homogeneity and limited residual internal stress, the polymerized denture undergoes no deformation with time, and is thus of improved fitting accuracy.

That is, it is only by using the resinous compositions for denture base according to the present invention, that homogeneous cured products and prepare therefrom dentures which are free from any internal porosity and of excellent fitting accuracy can be made possible.

What is claimed is:

1. A resinous composition for denture base, having improved performance suitable for microwave curing, which comprises in combination a two component composition comprised of:
   (i) a powdery component containing as the main constituents a methacrylate ester polymer having a mean particle size of 50 to 120 microns, a barbituric acid derivative and an organic peroxide, and
   (ii) a liquid component containing as the main constituents a monomethacrylate ester monomer, a crosslinking agent and a quaternary ammonium chloride.

2. A resinous composition as defined in claim 1, wherein the methacrylate ester polymer is a methyl methacrylate polymer.

3. A resinous composition as defined in claim 1, wherein the methacrylate ester polymer is a copolymer composed mainly of methyl methacrylate.

4. A resinous composition as defined in claim 1, wherein the methacrylate ester polymer is a mixture of a methyl methacrylate polymer with a copolymer composed mainly of methyl methacrylate.

5. A resinous composition as defined in claim 1, wherein the methacrylate ester polymer is a mixture of a methyl methacrylate polymer with a methacrylate ester polymer other than methyl methacrylate.

6. A resinous composition as defined in claim 1, wherein the methacrylate ester polymer is a mixture of a methyl methacrylate polymer with a copolymer of a methacrylate ester other than methyl methacrylate.

7. A resinous composition as defined in claim 1, wherein the methacrylate ester polymer is a mixture of a copolymer composed mainly of methyl methacrylate with a polymer of a methacrylate ester other than methyl methacrylate.

8. A resinous composition as defined in claim 1, wherein the methacrylate ester polymer is a mixture of a copolymer composed mainly of methyl methacrylate with a copolymer of a methacrylate ester other than methyl methacrylate.

9. A resinous composition as defined in claim 1, wherein the methacrylate ester polymer is a mixture of a methyl methacrylate polymer, a copolymer composed mainly of methyl methacrylate and a polymer of a methacrylate ester other than methyl methacrylate.

10. A resinous composition as defined in claim 1, wherein the methacrylate ester polymer is a mixture of a methyl methacrylate polymer, a copolymer composed mainly of methyl methacrylate and a copolymer of a methacrylate ester other than methyl methacrylate.

11. A resinous composition as defined in claim 1, wherein the barbituric acid derivative is one or more of 4-n-butylbarbituric acid, 1-benzyl-5-phenylbarbituric acid and 1-cyclohexyl-5-ethylbarbituric acid.

12. A resinous composition as defined in claim 1, wherein the organic peroxide is benzoyl peroxide, dilauroyl peroxide, or a mixture thereof.

13. A resinous composition as defined in claim 1, wherein 0.05 to 1 weight part of the barbituric acid derivative and 0.1 to 2 weight parts of the organic peroxide are used per 100 weight parts of the methacrylate ester polymer.

14. A resinous composition as defined in claim 1, wherein the monomethacrylate ester monomer is a methyl methacrylate monomer or a mixture of a methyl methacrylate monomer with a monomethacrylate ester monomer other than said methyl methacrylate monomer.

15. A resinous composition as defined in claim 1, wherein the crosslinking agent is one or more selected from the group consisting of polyfunctional methacrylates.

16. A resinous composition as defined in claim 1, wherein the crosslinking agent is one or more selected from the group consisting of polyfunctional methacrylates and a diallyl phthalate.

17. A resinous composition as defined in claim 1, wherein the crosslinking agent is a diallyl phthalate.

18. A resinous composition as defined in claim 1, wherein the quaternary ammonium chloride is one or more selected from the group consisting of lauryldimethylbenzylammonium chloride, dilauryldimethylammonium chloride and dioctyldimethylammonium chloride.

19. A resinous composition as defined in claim 1, wherein 0.1 to 15 weight parts of the cross-linking agent and 0.05 to 1 weight part of the quaternary ammonium chloride are used per 100 weight parts of the monomethacrylate ester monomer.

20. A denture base prepared from a resinous composition according to claim 1.

* * * * *